(12) United States Patent
Brock et al.

(10) Patent No.: US 6,318,193 B1
(45) Date of Patent: Nov. 20, 2001

(54) APPARATUS FOR USE IN SAMPLING AGGREGATE

(75) Inventors: J. Donald Brock, Chattanooga, TN (US); R. Ronald Collins, Mansfield; Michael E. Barrett, Lula, both of GA (US)

(73) Assignee: Pavement Technology, Inc., Covington, GA (US)

( * ) Notice: Subject to any disclaimer, the term of this patent is extended or adjusted under 35 U.S.C. 154(b) by 0 days.

(21) Appl. No.: 09/521,030

(22) Filed: Mar. 7, 2000

Related U.S. Application Data

(63) Continuation-in-part of application No. 09/168,922, filed on Oct. 8, 1998, now Pat. No. 6,062,093.

(51) Int. Cl.[7] .................................................. G01N 1/08
(52) U.S. Cl. ............................................................ 73/864.74
(58) Field of Search ........................... 73/864.31, 864.44, 73/864.45, 864.51, 864.62–864.64, 864.67, 864.73, 864.74

(56) References Cited

U.S. PATENT DOCUMENTS

| | | |
|---|---|---|
| 703,233 | 6/1902 | Brown . |
| 3,459,048 | 8/1969 | Bicknell . |
| 3,954,013 | 5/1976 | West . |
| 4,037,476 | 7/1977 | McCrabb . |
| 4,072,059 | 2/1978 | Hamilton . |
| 4,179,929 | * 12/1979 | Redding .............................. 73/864.31 |
| 4,346,612 | * 8/1982 | Rand ................................... 73/864.44 |
| 4,616,515 | 10/1986 | Dancoine . |
| 4,800,765 | * 1/1989 | Nelson ............................... 73/864.64 |
| 5,606,139 | * 2/1997 | Wittig et al. ...................... 73/864.44 |

OTHER PUBLICATIONS

"Standard Practice for Sampling Bituminous Paving Mixtures", ASTM Designation: D 979–96, pp. 96–98, No Date.
"GSP–15 Sampling Procedures for Asphaltic Concrete Mixtures", Georgia Department of Transportation, Jun. 1989, pp. 1–3.

(List continued on next page.)

*Primary Examiner*—Robert Raevis
(74) *Attorney, Agent, or Firm*—Chambliss, Bahner & Stophel, P.C.

(57) ABSTRACT

A sample collector for aggregate material is provided. The collector includes a support frame having a first end and a second end. A pair of guide plates are attached to the first end of the support frame. These guide plates are spaced apart so as to define a collection space therebetween. At least one of the guide plates is provided with a track that extends generally along the periphery of the collection space. A flexible closing plate is disposed between the guide plates and is adapted for sliding engagement with the track, so that the closing plate may be moved between an open position which exposes the collection space and a closed position which encloses the collection space. A mechanism is also provided for sliding the closing plate between the open position and the closed position.

20 Claims, 9 Drawing Sheets

OTHER PUBLICATIONS

"Sampling Hot Plant Mix Material", Wyoming Department of Transportation, Mar. 1996.

Plant Sampling Procedures, Illinois Department of Transportation, pp. 4–18 and 4–21, Jan. 1993.

"Procedures for Field Testing Hot–Mix Asphalt Under MDOT's Quality Management Program: MT–77", Mississippi Department of Transportation Standard Operating Procedures, Dec. 1996.

"Sampling HMA", Indiana Test Method or Procedure No. 580–97M, Indiana Department of Transportation Materials and Tests Division, revised Nov. 24, 1997.

"Sampling Bituminous Paving Mixtures", Kentucky Method 64–425–95; "Sampling Of Aggregates For Use As Highway Materials", Kentucky Method 64–601–95, No Date.

"Procedures for Sampling Stockpiled Aggregates", Indiana Test Method or Procedure No. 207–87M, Indiana Department of Transportation Materials and Tests Division, revised Feb. 14, 1996.

"Standard Practice for Sampling Aggregates", ASTM Designation: D 75–87(Reapproved 1992), pp. 16–19, Sep. 1992.

* cited by examiner

APPARATUS FOR USE IN SAMPLING AGGREGATE

CROSS-REFERENCE TO RELATED APPLICATIONS

This application is a continuation-in-part of the copending application entitled "Method And Apparatus For Sampling Aggregate Material" which was filed on Oct. 8, 1998 and assigned a Ser. No. of 09/168,922, now U.S. Pat. No. 6,062,093 the disclosure of which is fully incorporated herein by reference.

FIELD OF THE INVENTION

This invention relates generally to the sampling of aggregate materials, especially to the sampling of such materials from a truck, railcar, barge or other conveyance. A preferred embodiment of the invention provides an apparatus for the sampling of bituminous paving materials.

BACKGROUND AND DESCRIPTION OF THE PRIOR ART

Sampling of various aggregate materials is commonly required in the construction and mining industries to insure that the materials meet the required specifications for quality, composition and/or gradation. Samples of the aggregate product may be taken at various stages in the process from production or manufacture to delivery to the customer. Samples may be taken from stockpiles, silos or other storage facilities, or they may be taken from trucks, barges, railcars, conveyors or other transport vehicles or devices.

It is common for producers of aggregate materials to sample their product at several stages, including the shipping stage. In addition, the purchaser will almost always sample at least a portion of the incoming shipments before unloading them to insure that they are acceptable. Aggregate materials that are hauled by truck are usually sampled by hand shoveling a sample portion from various locations in the aggregate load in the truck bed, in order to obtain a representative sample. Because the aggregate may segregate by size as it is being loaded and hauled, however, hand sampling in this way makes it difficult to obtain a representative sample. It is generally necessary to remove a portion of the surface material from several locations in the truck bed in order to obtain a sample portion from therebeneath. However, when the aggregate material is bituminous paving material such as asphalt concrete, its surface temperature may be as high as 250–300° F., which makes hand sampling at least uncomfortable and potentially dangerous. Furthermore, a worker who is charged with the responsibility of obtaining a hand sample from an asphalt concrete truck will not likely be willing and may not be able to spend the time to take sample portions from various locations on the load in the truck bed to insure that he gets a representative sample. Nevertheless, the standard practice for sampling bituminous paving mixtures from truck transports is to take several portions of a sample from each truck using a flat-bottom scoop or a square-nose shovel.

ASTM Designation D 979-96 specifies that at least three approximately equal increments should be taken from each truck load of bituminous paving materials sampled. Various state highway departments impose additional requirements on the sampler of asphalt concrete, in an effort to insure that representative samples are obtained. For example, the Georgia Department of Transportation Sampling Procedure GSP-15 specifies that hand samples may be taken only after the "cone" of material in the bed of the truck is first shoveled off to a depth such that the resulting flat area is at least 60% as wide as the truck and at least six inches deep. Wyoming Department of Transportation Sampling Procedure 830.0 requires that for smaller trucks, a sample area must be prepared by removing the top 2–4 inches from each quarter of the load, while for larger trucks, at least two transverse trenches must be excavated across the load in the truck bed. The sample is then removed by pushing the shovel into each cleared area or trench at a 45° angle. Illinois Department of Transportation Sampling Procedure 4.7.1 requires that an equal amount of material is to be taken from locations approximately one foot below the top of each pile in the truck bed, at quarter points around the pile's circumference. Mississippi Department of Transportation Field Testing Procedure TMD-11-77-00-000 requires that at least three samples be taken from specified locations in the truck after first removing the top 2–3 inches of material at each sample point. All of these procedures require that the sampler work for a significant period of time in the bed of the truck atop the load of hot asphalt concrete. Complying with such procedures is uncomfortable and may be dangerous, which makes proper sampling problematic.

It would be desirable therefore if an apparatus could be developed that would permit the taking of samples from a truck or other conveyance quickly and safely. It would also be desirable if such apparatus would eliminate the need for the worker charged with obtaining the sample to climb into the truck bed and onto the load therein.

ADVANTAGES OF THE INVENTION

Among the advantages of the invention claimed herein is that the sample collector for aggregate material may be operated to obtain a representative sample of such material without requiring removal of the surface layer of material being sampled. Another advantage is that the sample collector may be operated remotely so that a worker that is charged with obtaining a sample from a truck or other means of conveyance is not required to climb onto the load of material to obtain the sample.

Additional advantages of this invention will become apparent from an examination of the drawings and the ensuing description.

EXPLANATION OF TECHNICAL TERMS

As used herein, aggregate materials refers to particulate materials that may be transported in bulk, including bituminous paving mixtures such as hot-mix asphalt and cold mix, crushed limestone and other types of stone, gravel, sand, lime, coal, coke, fertilizer, grain, pellets and similar materials.

As used herein, bituminous paving mixtures refers to mixtures of various aggregates, including crushed stone, sand, lime and the like, with asphalt cement or asphalt binder, which mixtures are prepared for paving purposes.

As used herein, asphalt cement or asphalt binder refers to a black or brown tar-like substance, a type of bitumen that occurs naturally or is obtained from the distillation of coal tar, wood tar or petroleum.

As used herein, asphalt concrete refers to a bituminous paving mixture that is prepared, using hot asphalt cement or asphalt binder, in a hot-mix asphalt plant. A synonymous term is hot-mix asphalt.

As used herein, cold mix refers to a bituminous paving mixture that is prepared without the use of hot asphalt cement or asphalt binder.

As used herein, sampler refers to a person who is charged with the responsibility for taking or collecting samples of aggregate material.

SUMMARY OF THE INVENTION

The invention comprises a sample collector for aggregate material, and includes a support frame having a first end and a second end. A pair of guide plates are attached to the first end of the support frame. These guide plates are spaced apart so as to define a collection space therebetween. At least one of the guide plates is provided with a track that extends generally along the periphery of the collection space. A flexible closing plate is disposed between the guide plates and is adapted for sliding engagement with the track, so that the closing plate may be moved between an open position which exposes the collection space and a closed position which encloses the collection space. Means are also provided for sliding the closing plate between the open position and the closed position.

In order to facilitate an understanding of the invention, the preferred embodiments of the invention are illustrated in the drawings, and a detailed description thereof follows. It is not intended, however, that the invention be limited to the particular embodiments described or to use in connection with the apparatus illustrated herein. Various modifications and alternative embodiments such as would ordinarily occur to one skilled in the art to which the invention relates are also contemplated and included within the scope of the invention described and claimed herein.

BRIEF DESCRIPTION OF THE DRAWINGS

The presently preferred embodiments of the invention are illustrated in the accompanying drawings, in which like reference numerals represent like parts throughout, and in which.

DESCRIPTION OF THE PREFERRED EMBODIMENTS OF THE INVENTION

Figure 1:
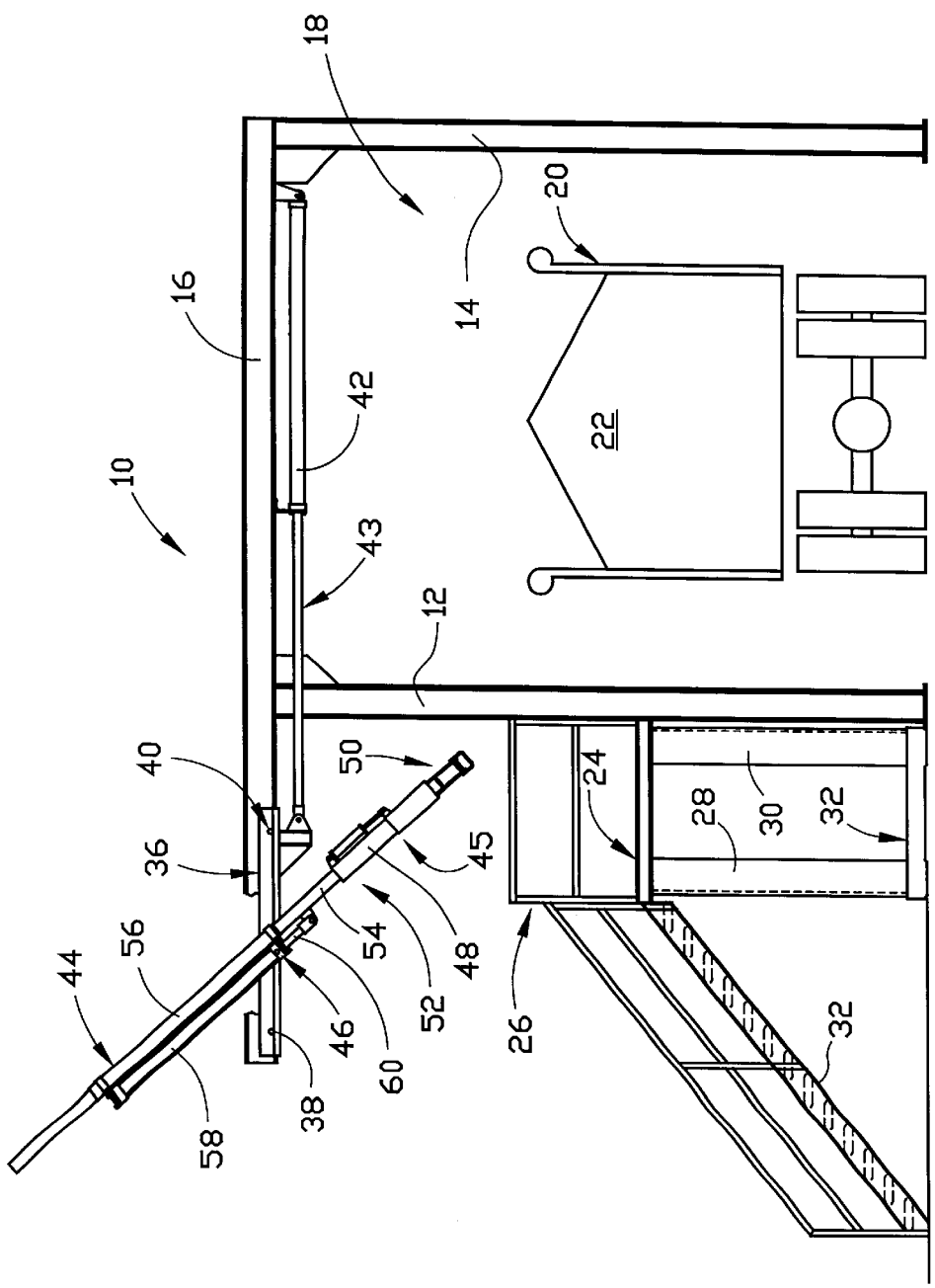
FIG. 1 is a front view of a sample collector assembly according to the invention that is adapted for sampling of aggregate materials from a conveyance such as a truck.
Figure 2:
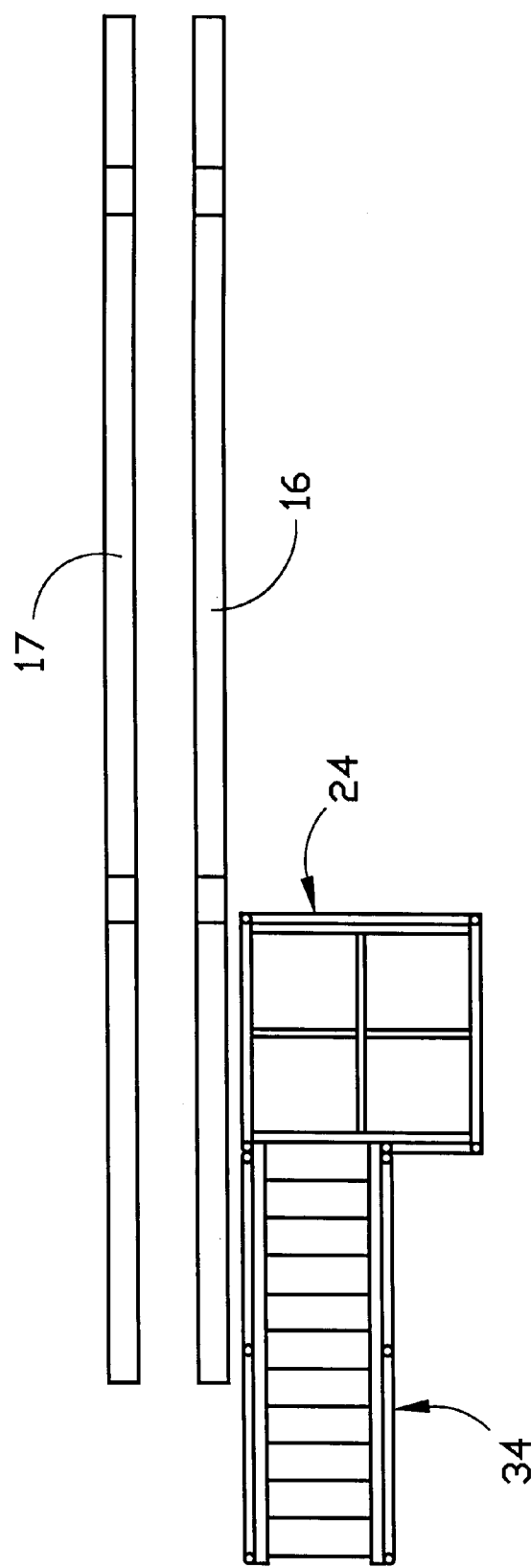
FIG. 2 is a top view of a portion of the assembly of FIG. 1.

Referring now to the drawings, FIGS. 1 and 2 illustrate a preferred embodiment of the invention, a sample collector assembly that is adapted for sampling of aggregate materials from a conveyance such as a truck. As shown therein, assembly 10 includes frame portions 12, 14, 16 and 17 (FIG. 2), preferably made of steel or other suitable material, that generally define a truck zone 18 into which truck 20, containing a load of aggregate material 22, may be driven. Of course, the frame of the assembly may be arranged in any convenient configuration, depending on whether the samples are to be taken from trucks, railcars, barges, conveyors or from stationary stockpiles.

Frame portions 16 (shown in partial cutaway in FIG. 1) and 17 define an overhead rail that is suspended over and adjacent to the truck zone. Platform 24 is also located adjacent to the truck zone, and is surrounded by safety rail 26. Platform 24 is elevated by support legs, including legs 28 and 30, which are mounted on base 32. Staircase 34 provides access to the platform from ground level. The platform may be utilized by an operator of the sample collector assembly, or the assembly may be operated remotely by use of a video camera and a remote collector actuator (not shown) such as are known to those having ordinary skill in the art to which the invention relates. If remote operation is desired, the assembly may also include a small elevator or other conveyor (also not shown) to transport a sample taken by the collector to a ground level collection station. Such an elevator may be mounted on or adjacent to frame portion 12.

Carriage 36 is adapted to ride on overhead rails 16 and 17 by means of rollers 38 and 40 between a first position adjacent to the truck zone (shown in FIG. 1) and at least one sampling position over the truck zone (not shown). Hydraulic cylinder 42 is mounted on the overhead rails and the carriage and is provided with piston 43 that is attached to the carriage so that the cylinder may move the carriage between the first position adjacent to the truck zone (shown in FIG. 1) and at least one sampling position over the truck zone. Of course, other means and mechanisms for moving the carriage between the first position and the sampling positions as are known to those skilled in the art to which the invention relates, as well as those subsequently developed, are also included within the invention.

Sample collector subassembly 44, including sample collector 45, is mounted on the carriage at mounting point 46. In one embodiment of the invention, the sample collector subassembly is mounted so as to pivot about mounting point 46. In this embodiment, it is preferred that the sample collector subassembly be mounted to pivot on the carriage so as to permit the sample collector to be inserted into the aggregate along an axis that is disposed at any angle within the range of about 30° to about 150° from the horizontal. In another embodiment of the invention, the sample collector subassembly may be mounted on carriage 36 at mounting point 46 at a fixed angle, such as at 60° from the horizontal. In yet another embodiment of the invention, the sample collector subassembly may be provided in the form of a portable unit that may be carried by the sampler, especially if it is used to sample stockpiled material.

FIGS. 3 through 7 illustrate a preferred embodiment of the sample collector in more detail. As shown therein, sample collector 45 includes support frame 48, having first end 50 and second end 52. It is generally preferred that the support frame be provided in the form of a length of tubing having a pair of generally planar sides, each of which is disposed generally parallel to the other. The support frame may be provided in a square, rectangular, hexagonal or other convenient cross-section. Preferably, as shown in FIGS. 3–7, frame 48 is a length of square tubing that is made of steel or other suitable material. As shown on FIG. 1, subassembly 44 also includes elongate extension 54, which is attached to the second end 52 of the support frame of collector 45, and boom 56, to which the elongate extension is mounted. These components are also preferably made from steel or other suitable material. Preferably extension 54 is mounted in sliding engagement within boom 56, and is adapted to telescope therefrom. Hydraulic cylinder 58 is attached to boom 56 and provided with piston 60, which is attached to extension 54, so that cylinder 58 may move extension 54 from a retracted position (shown in FIG. 1) to an extended position (not shown) for inserting collector 45 into the aggregate material in the truck. Of course, hydraulic cylinder 58 of the preferred embodiment of the invention that is illustrated in FIG. 1 may be replaced by other means for moving the extension with respect to the boom as are known to those having ordinary skill in the art to which the invention relates, or which may be subsequently developed.

A pair of guide plates 62 and 64 are attached to first end 50 of the support frame. The guide plates are spaced apart so as to define a collection space therebetween, and at least one of the guide plates is provided with a track that extends generally along the periphery of the collection space. Preferably each of the guide plates is provided with a pair of tracks 66A and 66B so that each track on a guide plate extends generally along one side of the periphery of the collection space to a common termination point 68, and so that the tracks on guide plate 62 (not shown) are generally parallel to the tracks on guide plate 64.

Figure 3:
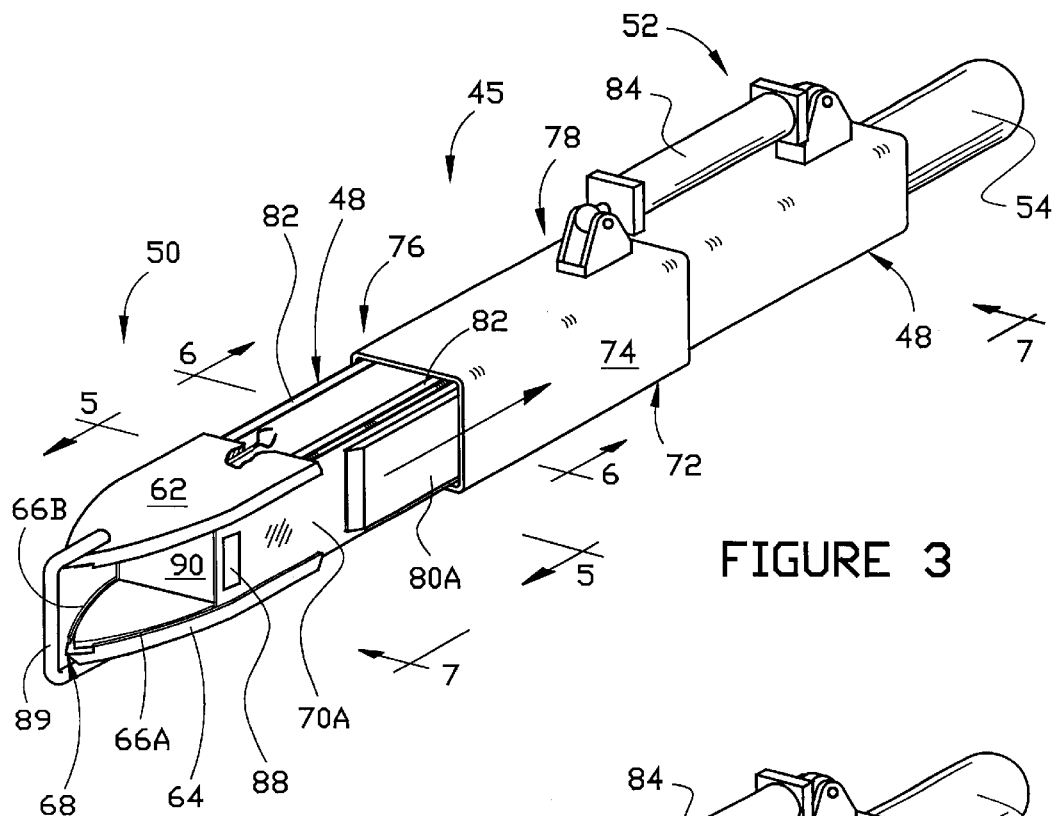
FIG. 3 is a perspective view of the sample collector that is a part of the assembly of FIG. 1, showing the closing plate in the open position, and including a partial sectional portion.
Figure 4:
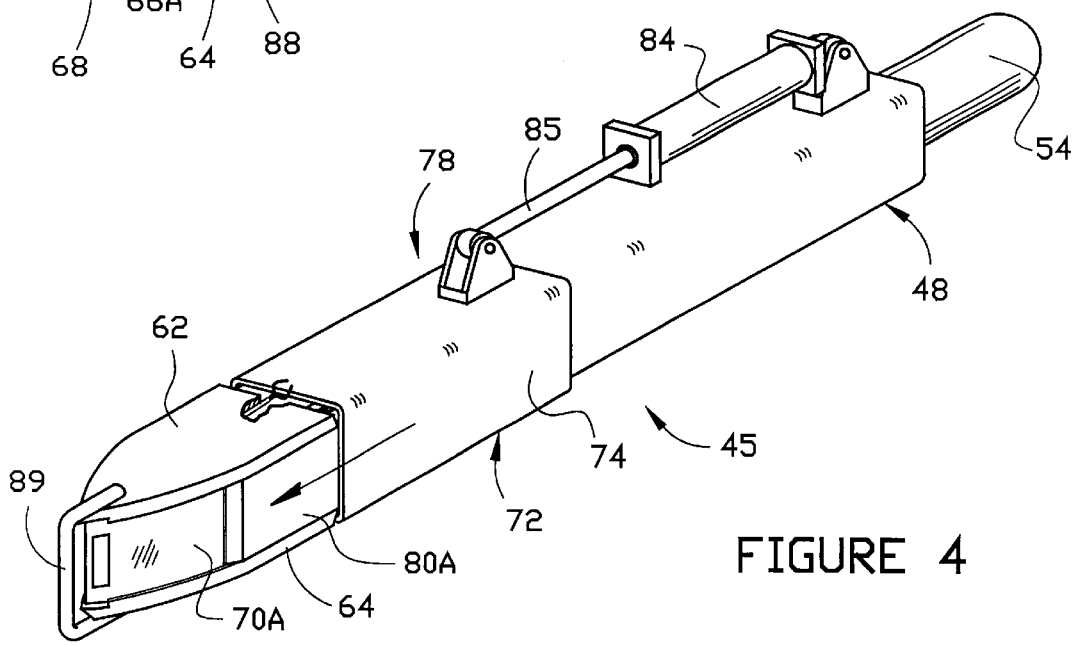
FIG. 4 is a perspective view of the sample collector illustrated in FIG. 3, but showing the closing plate in the closed position.
Figure 3A:
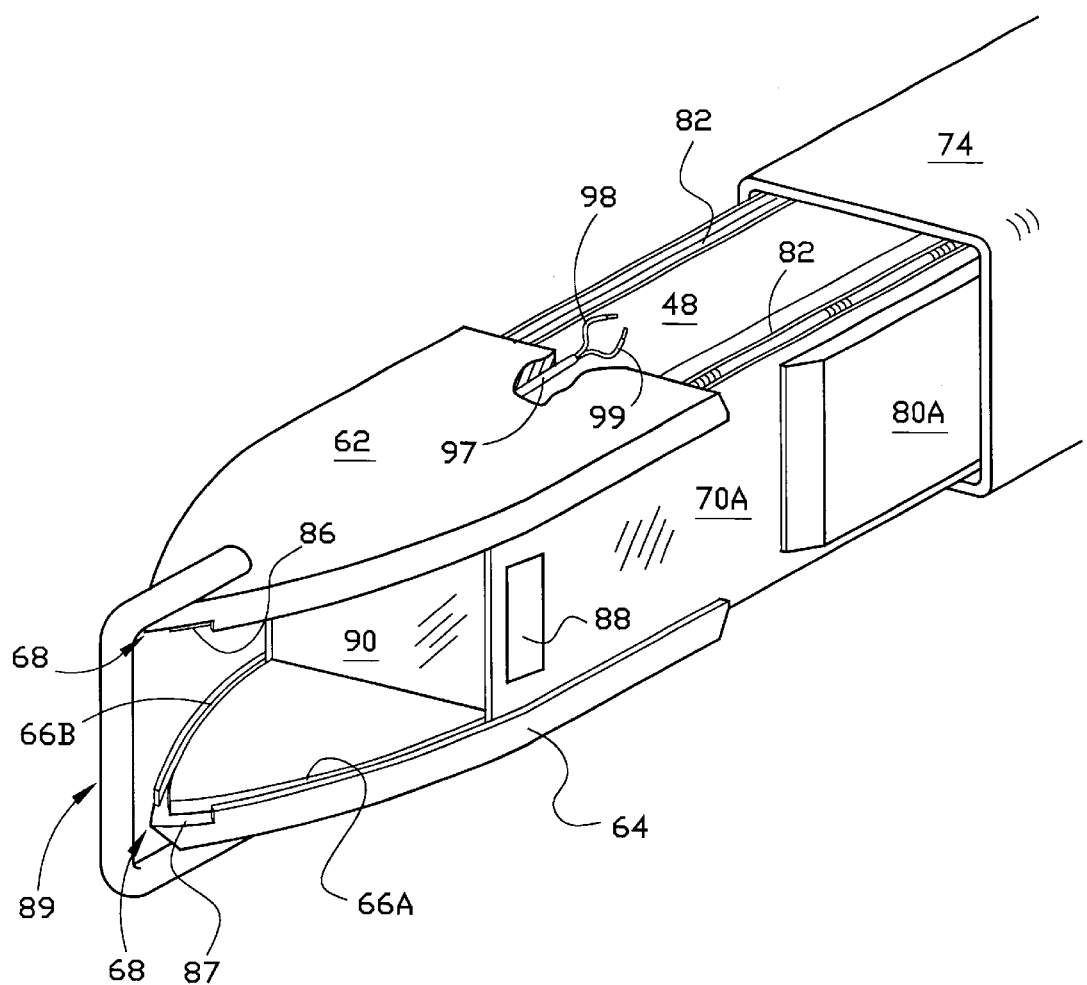
FIG. 3A is an enlarged view of a portion of the sample collector shown in FIG. 3.
Figure 4A:
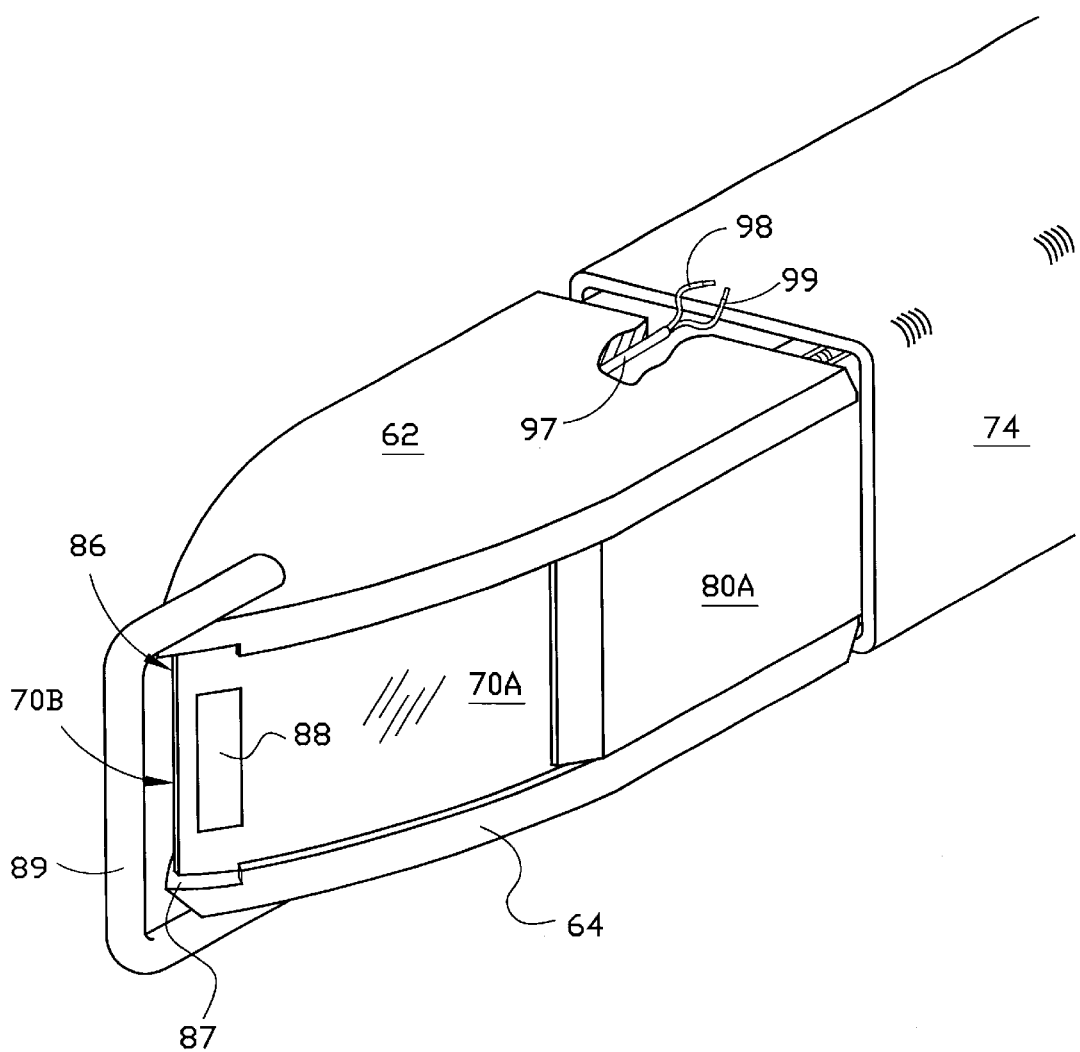
FIG. 4A is an enlarged view of a portion of the sample collector shown in FIG. 4.
Figure 6:
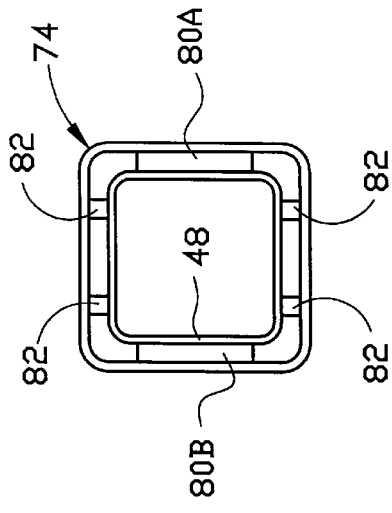
FIG. 6 is a partial cross-sectional view of the sample collector of FIG. 3, taken along the line 6—6.
Figure 5:
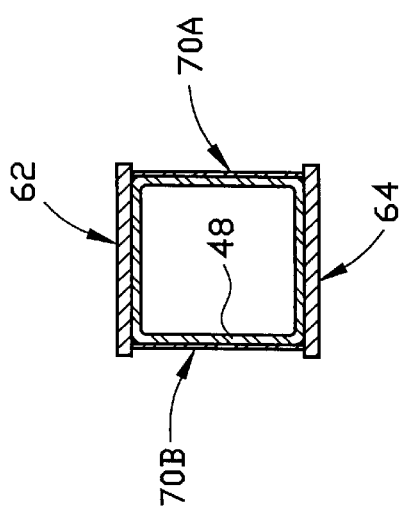
FIG. 5 is a cross-sectional view of the sample collector of FIG. 3, taken along the line 5—5.
Figure 12:
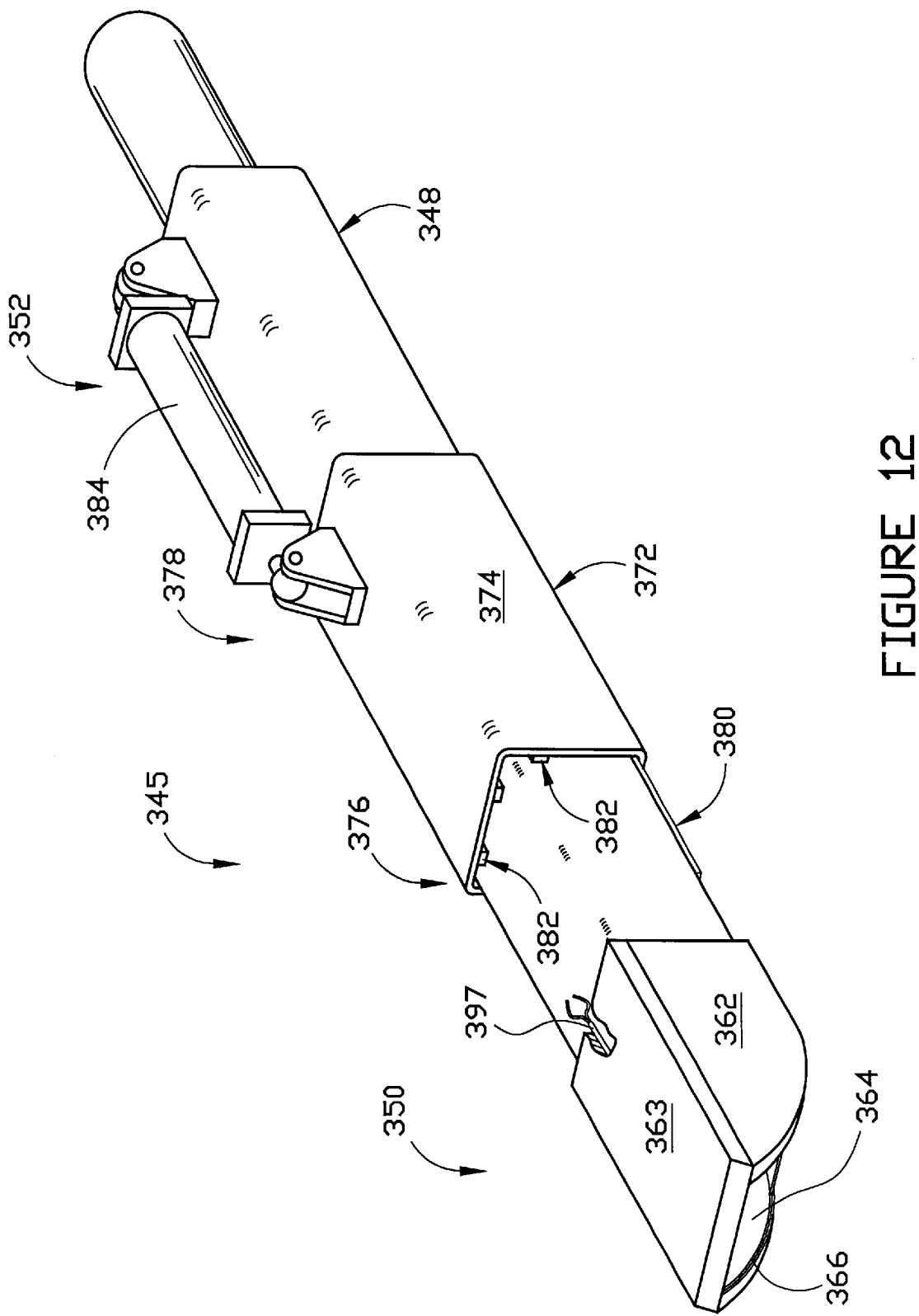
FIG. 12 is a perspective view of a third alternative embodiment of the sample collector of FIGS. 3–7, showing the closing plate in the open position, and including a partial sectional portion.

Sample collector 45 also includes at least one flexible closing plate which is disposed between the guide plates and adapted for sliding engagement with the track so that the closing plate may be moved between an open position which exposes the collection space and a closed position which encloses the collection space. Preferably, as shown in FIGS. 3, 3A, 4, 4A and 5, a pair of flexible closing plates 70A and 70B (see FIGS. 4A and 5) are provided. It is also preferred that the closing plates are attached to a carrier which is adapted to move along the support frame. As shown in FIGS. 3, 4 and 6, carrier 72 is preferably comprised of tubing component 74 having a first end 76 and a second end 78, to which (at first end 76) a pair of mounting plates 80A and 80B (see FIG. 6) are attached. Furthermore, the closing plates are preferably attached to the mounting plates on opposite sides of the carrier. Thus, as illustrated in FIGS. 3 and 4, flexible closing plate 70A is attached to mounting plate 80A. It is generally preferred that the carrier be provided in the form of or include a length of tubing having a pair of generally planar sides, each of which is disposed generally parallel to the other. As is the case with respect to the support frame, the carrier tubing component may be provided in a square, rectangular, hexagonal or other convenient cross-section. Preferably, as shown in FIGS. 3, 4 and 6, tubing component 74 of carrier 72 is a length of square tubing that is made of steel or other suitable material. Obviously, if support frame 48 and tubing component 74 of carrier 72 are provided in the telescoping relationship illustrated in the drawings, their shapes must be compatible with such physical arrangement. Furthermore, in order that tubing component 74 may easily slide outside of support frame 48, glide strips 82 are preferably provided between component 74 and frame 48. These glide strips are preferably made of steel or other suitable material and may be applied either to the outer surface of support frame 48, as shown in FIGS. 3 and 6, or to the inner surface of the tubing component of the carrier, as shown in FIG. 12 (as subsequently described).

Carrier 72 is adapted to move along support frame 48 between an open position in which the closing plates expose the collection space and a closed position in which the closing plates enclose the collection space. Preferably, such motion is actuated by hydraulic cylinder 84. As shown in FIG. 4, hydraulic cylinder 84 includes piston 85 which is attached to second end 78 of tubing component 74 of carrier 72. The cylinder is also preferably attached to support frame 48 so that extension of piston 85 from cylinder 84 (or retraction of piston 85 into cylinder 84) will move tubing component 74 of carrier 72 with respect to the support frame between an open position in which the closing plates expose the collection space (FIG. 3) and a closed position in which the closing plates enclose the collection space (FIG. 4). Of course, hydraulic cylinder 84 of the preferred embodiment of the invention that is illustrated in the drawings may be replaced by other means for moving the carrier with respect to the support frame as are known to those having ordinary skill in the art to which the invention relates or which may be subsequently developed.

It is preferred that each of tracks 66A and 66B comprises a groove in the guide plate into which the closing plates may be fitted in sliding engagement, although other track configurations such as a raised rail (not shown) may also be employed. Obviously whatever track configuration is employed, the closing plates will have to be compatible therewith so that sliding engagement will be maintained. It is contemplated that the term "sliding engagement" as used herein to describe the relationship between a closing plate and its associated track includes rolling engagement such as where the track is provided in the form of a raised rail and the closing plate is fitted with wheels that roll on either side thereof. In the preferred embodiment of FIGS. 3 and 4, however, both of the tracks in each guide plate are provided in the form of grooves. In addition, relief openings 86 and 87 are provided in guide plates 62 and 64 respectively (best shown in FIGS. 3A and 4A) in order that closing movement of the closing plates may purge the tracks of any sample material that may have accumulated therein when sample collector 45 is plunged into the material to be sampled. Such relief openings are particularly useful when the collector is used to sample sticky material such as bituminous paving mixtures. This embodiment of the invention also includes a reinforcing strip 88 mounted onto the leading edge of each of the closing plates (only one of which is illustrated in the drawings). These reinforcing strips, which are preferably made of steel, serve to minimize deflection of the closing plates as they close around a sample of aggregate. In addition, nose guard 89, preferably of steel, is mounted to guide plates 62 and 64 adjacent to common termination point 68 in order to provide additional protection for the closing plates.

Figure 7:
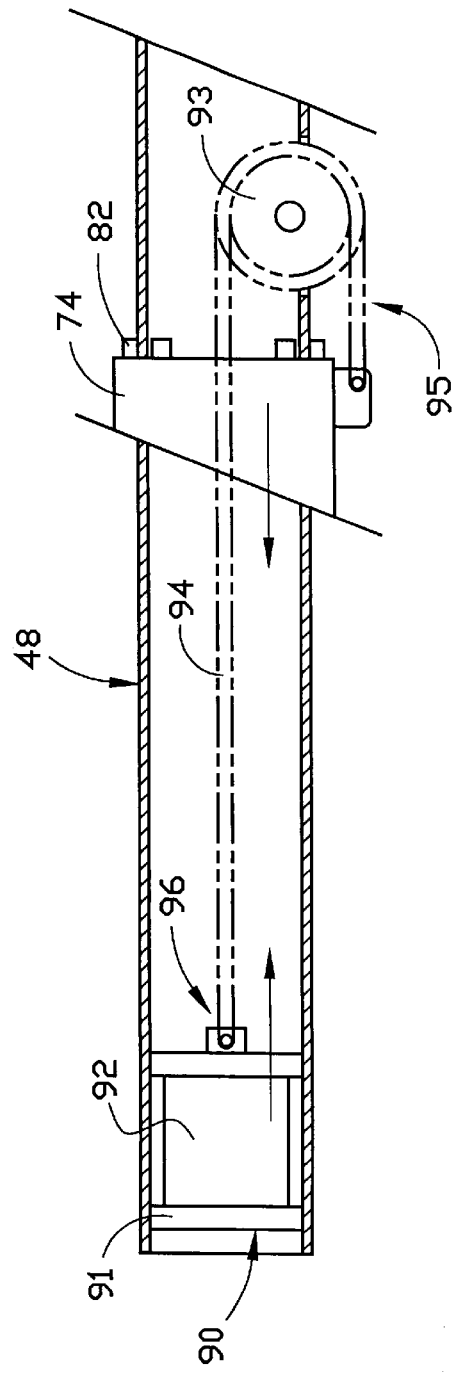
FIG. 7 is a partial cross sectional view of the sample collector of FIG. 3, taken along the line 7—7.

Another feature of a preferred embodiment of the invention that may be particularly useful when the invention is employed to sample bituminous paving mixtures is sample extraction plate 90 that is disposed between the guide plates and which is adapted to push the sample out of the collection space. As illustrated in FIG. 7, it is preferred that the extraction plate be constructed of thick steel plate 91 to which a block or piece of thick tubing 92 is attached for added mass. In the preferred embodiment of the invention, the extraction plate is adapted to conform to the inside shape of support frame 48, but must be capable of moving between the guide plates so as to push the sample out of the collection space. As shown in schematic form in FIG. 7, it is also preferred that a wheel such as sprocket 93 be mounted within the support frame, and that a belt such as roller chain 94 be provided and disposed around the sprocket. The roller chain has a first end 95 that is attached to the second end 78 of tubing component 74 of carrier 72, and a second end 96 that is attached to the sample extraction plate, or to the block or tubing 92 which is attached to the extraction plate.

Another feature of the preferred embodiment of the invention that is particularly useful in sampling hot-mix asphalt is heater 97 (best shown in FIGS. 3A and 4A) that is provided in at least one, and preferably both of the guide plates 62 and 64. Heater 97 is preferably a commercially available cartridge heater that is available from a number of sources, and may be connected to an electrical source by means of wires 98 and 99. The heater may be used to minimize sticking of hot-mix asphalt on the guide plates during the sampling process.

In the practice of the embodiment of the invention illustrated in FIGS. 1–7, truck 20 is driven into truck zone 18. Carriage 36 with sample collector subassembly 44 mounted thereon is moved by the action of cylinder 42 from the first position adjacent to the truck zone to a sampling position over the truck zone. Sample collector subassembly 44 is then pivoted (if pivotally mounted on carriage 36) about mounting point 46 to the desired angle, preferably at about 60° from the horizontal.

Cylinder extension 54 may then be moved with respect to boom 56 by the action of cylinder 58 from a retracted position to an extended position so as to insert the collector into the aggregate material in the truck. Preferably, the collector is inserted so that the collection space is imbedded to a depth of at least about twelve inches in the material in the truck before the closing plates are opened to expose the collection space. This depth is preferred because the outer layers of material in the truck tend to become segregated as the truck is loaded. Consequently, a sample that is more likely representative of the entire load may be obtained from a depth beneath the surface layer of the aggregate. When the collector is placed in the desired position, piston 85 may be moved by the action of cylinder 84 to move carrier 72 back (along the arrow of FIG. 3) to the open position in which the closing plates expose the collection space. Cylinder extension 54 may then be moved with respect to boom 56 by the action of cylinder 58 so as to insert the collector further into the aggregate material in the truck. In the alternative, although not preferred, the collector may be placed in the aggregate with the closing plates in the open position to expose the collection space. As the collector is pushed further into the aggregate material (or alternatively, is pushed into the aggregate material), extraction plate 90 will be pushed to the back of the collection space and into support tubing 48. Piston 85 may then be moved by the action of cylinder 84 to move carrier 72 forward (along the arrow of FIG. 4, and to the left as viewed in FIG. 7) to the closed position in which the closing plates enclose the collection space. As this occurs, extraction plate 90 is pulled back (to the right as viewed in FIG. 7) by roller chain 94 out of the collection space and into the support tubing, permitting the sample material to enter the collection space. Cylinder 58 may then be actuated to move extension 54 from the extended position to a retracted position to withdraw the collector from the aggregate material in the truck. Cylinder 42 may then be actuated to move the carriage to the first position adjacent to the truck zone. The collector subassembly 44 may be rotated (if necessary) to the preferred sample ejection position (not shown), typically at an angle of 45–60° from the horizontal. Piston 85 may then be moved by cylinder 84 to move the carrier back to the open position in which the closing plates expose the collection space. As this occurs, ejection plate 90 is moved forward under the influence of gravity to push the sample out of the collector. Additional samples may then be taken, if desired, from other locations in the truck bed, by changing the angle, the location and/or the depth at which the probe is inserted into the aggregate, as well as by moving the truck within the truck zone, if desired.

Figure 8:
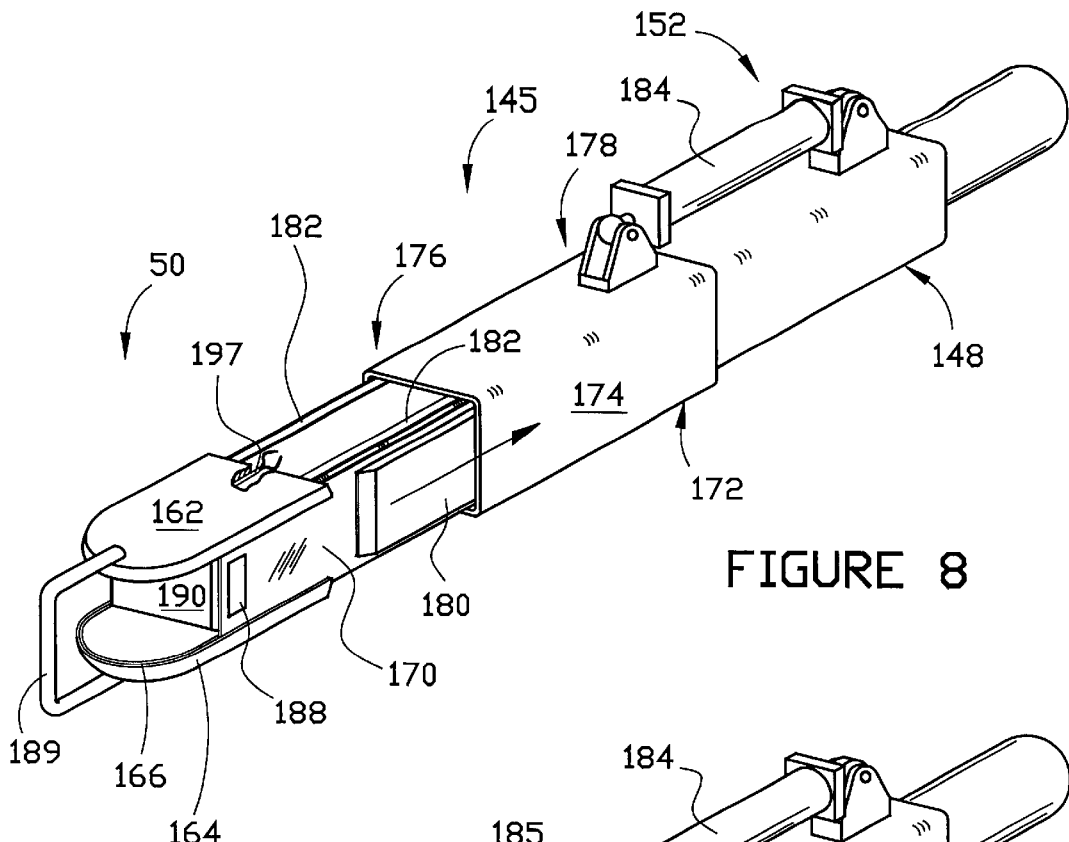
FIG. 8 is a perspective view of a first alternative embodiment of the sample collector of FIGS. 3–7, showing the closing plate in the open position, and including a partial sectional portion.
Figure 9:
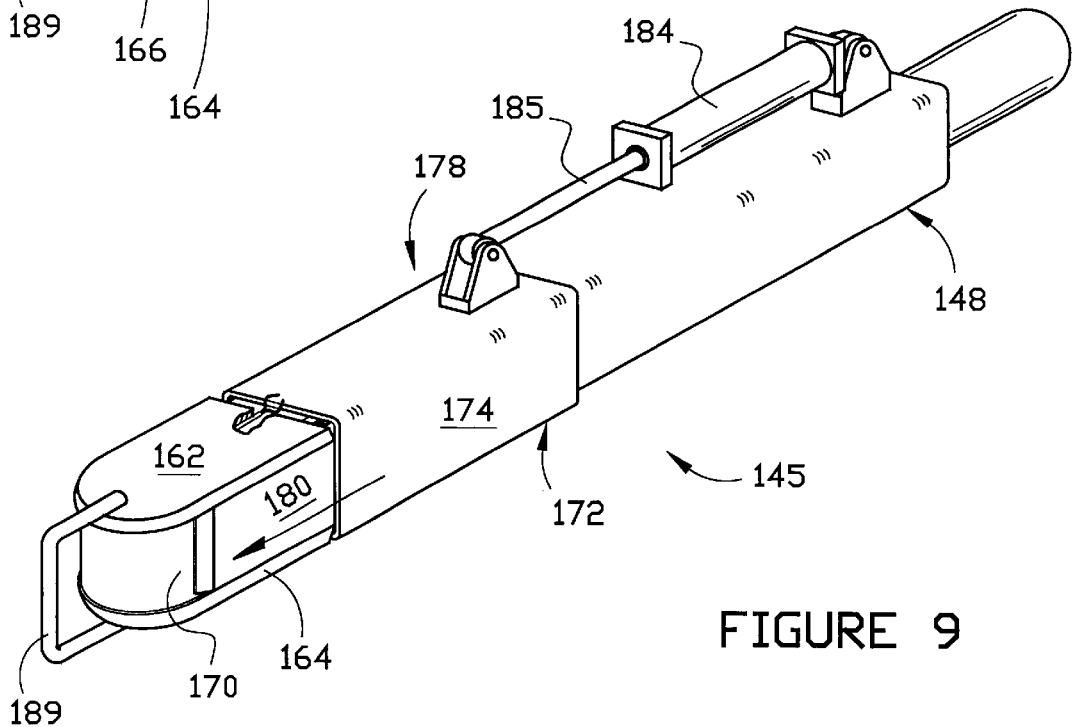
FIG. 9 is a perspective view of the sample collector of FIG. 8, showing the closing plate in the closed position.

FIGS. 8 and 9 illustrate a second embodiment 145 of the sample collector, in which a single closing plate 170 is employed. Such an embodiment may be particularly useful in sampling lightweight aggregate that is less viscous or "sticky" than bituminous paving materials. Sample collector 145 includes support frame 148, having first end 150 and second end 152. Support frame 148 is provided in the form of a length of square tubing that is made of steel or other suitable material. A pair of guide plates 162 and 164 are attached to first end 150 of the support frame. The guide plates are spaced apart so as to define a collection space therebetween, and preferably each of the guide plates is provided with a track 166 that extends generally along the periphery of the collection space so that the track on guide plate 162 (not shown) is generally parallel to the track on guide plate 164.

Sample collector 145 also includes flexible closing plate 170 which is disposed between the guide plates and adapted for sliding engagement with the track so that the closing plate may be moved between an open position which exposes the collection space and a closed position which encloses the collection space. Preferably, as shown in the drawings, track 166 comprises a groove in the guide plate into which the closing plate may be fitted in sliding engagement. Closing plate 170 is attached to a carrier which is adapted to move along the support frame. Carrier 172 is preferably comprised of tubing component 174 having a first end 176 and a second end 178. In this embodiment of the invention, mounting plate 180 is attached to tubing component 174 at first end 176, and closing plate 170 is attached to the mounting plate. Preferably, tubing component 174 of carrier 172 is a length of square tubing that is made of steel or other suitable material. In order that tubing component 174 may easily slide outside of support frame 148, glide strips 182 are provided on the outer surface of frame 148.

Carrier 172 is adapted to move along support frame 148 between an open position in which the closing plate exposes the collection space and a closed position in which the closing plate encloses the collection space. Preferably, such motion is actuated by hydraulic cylinder 184. As shown in FIG. 9, hydraulic cylinder 184 includes piston 185 which is attached to second end 178 of tubing component 174 of carrier 172. The cylinder is also preferably attached to support frame 148 so that extension of piston 185 from cylinder 184 (or retraction of piston 185 into cylinder 184) will move tubing component 174 of carrier 172 with respect to the support frame between an open position in which the closing plate exposes the collection space (FIG. 8) and a closed position in which the closing plate encloses the collection space (FIG. 9). This embodiment of the invention also includes a reinforcing strip 188 mounted onto the leading edge of the closing plate (see FIG. 8), in order to minimize deflection of the closing plate as it closes around a sample of aggregate. In addition, nose guard 189 is mounted to guide plates 162 and 164 in order to provide additional protection for the closing plate. Sample extraction plate 190 is disposed between the guide plates and is adapted to push the sample out of the collection space in much the same way that sample extraction plate 90 pushes a sample out of the collection space of collector 45. This embodiment of the invention also includes heater 197 that is provided in at least one, and preferably both of the guide plates 162 and 164.

Figure 10:
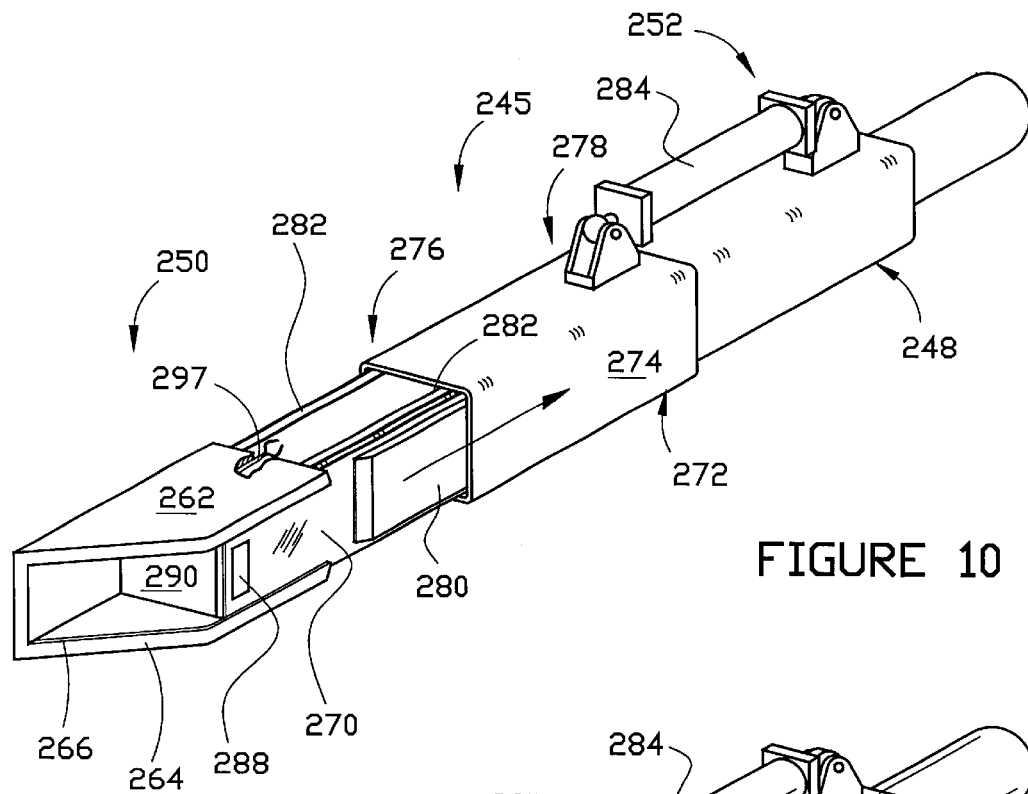
FIG. 10 is a perspective view of a second alternative embodiment of the sample collector of FIGS. 3–7, showing the closing plate in the open position, and including a partial sectional portion.
Figure 11:
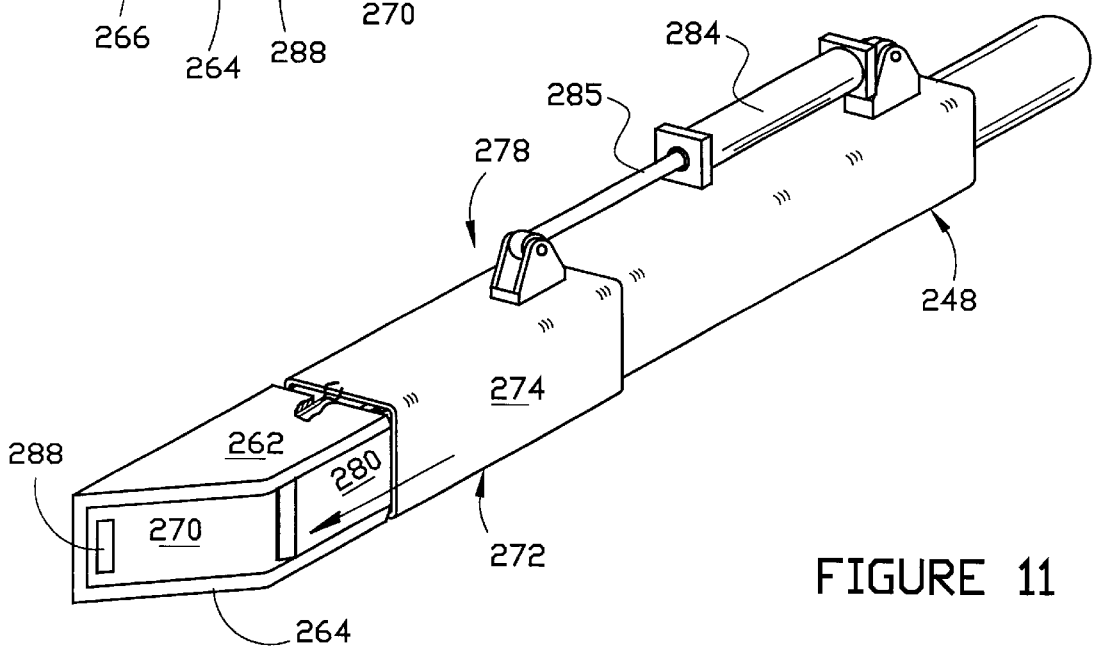
FIG. 11 is a perspective view of the sample collector of FIG. 10, showing the closing plate in the closed position.

FIGS. 10 and 11 illustrate a third embodiment 245 of the sample collector, in which, like collector 145, a single closing plate is employed. Sample collector 245 includes support frame 248, having first end 250 and second end 252. Support frame 248 is provided in the form of a length of square tubing that is made of steel or other suitable material. A pair of guide plates 262 and 264 are attached to first end 250 of the support frame. The guide plates are spaced apart so as to define a collection space therebetween, and preferably each of the guide plates is provided with a track 266 that extends generally along the periphery of the collection space so that the track on guide plate 262 (not shown) is generally parallel to the track on guide plate 264.

Sample collector 245 also includes flexible closing plate 270 which is disposed between the guide plates and adapted for sliding engagement with the track so that the closing plate may be moved between an open position which exposes the collection space and a closed position which encloses the collection space. Preferably, as shown in the drawings, track 266 comprises a groove in the guide plate into which the closing plate may be fitted in sliding engagement. Closing plate 270 is attached to a carrier which is adapted to move along the support frame. Carrier 272 is preferably comprised of tubing component 274 having a first end 276 and a second end 278. In this embodiment of the invention, mounting plate 280 is attached to tubing component 274 at first end 276, and closing plate 270 is attached to the mounting plate. Preferably, tubing component 274 of carrier 272 is a length of square tubing that is made of steel or other suitable material. In order that tubing component 274 may easily slide outside of support frame 248, glide strips 282 are provided on the outer surface of frame 248.

Carrier 272 is adapted to move along support frame 248 between an open position in which the closing plate exposes the collection space and a closed position in which the closing plate encloses the collection space. Preferably, such motion is actuated by hydraulic cylinder 284. As shown in FIG. 11, hydraulic cylinder 284 includes piston 285 which is attached to second end 278 of tubing component 274 of carrier 272. The cylinder is also preferably attached to support frame 248 so that extension of piston 285 from cylinder 284 (or retraction of piston 285 into cylinder 284) will move tubing component 274 of carrier 272 with respect to the support frame between an open position in which the closing plate exposes the collection space (FIG. 10) and a closed position in which the closing plate encloses the collection space (FIG. 11). This embodiment of the invention also includes a reinforcing strip 288 mounted onto the leading edge of the closing plate, in order to minimize deflection of the closing plate as it closes around a sample of aggregate. Sample extraction plate 290 is disposed between the guide plates and is adapted to push the sample out of the collection space in much the same way that sample extraction plate 90 pushes a sample out of the collection space of collector 45. This embodiment of the invention also includes heater 297 that is provided in at least one, and preferably both of the guide plates 262 and 264.

FIG. 12 illustrates a fourth embodiment 345 of the sample collector which is very similar to sample collector 245. Sample collector 345 includes support frame 348, having first end 350 and second end 352. Support frame 348 is provided in the form of a length of square tubing that is made of steel or other suitable material. A pair of guide plates 362 and 364 are attached with top plate 363 therebetween to first end 350 of the support frame. The guide plates are spaced apart so as to define a collection space therebetween, and preferably each of the guide plates is provided with a track 366 that extends generally along the periphery of the collection space so that the track on guide plate 362 (not shown) is generally parallel to the track on guide plate 364.

Sample collector 345 also includes a flexible closing plate (not shown) which is disposed between the guide plates and adapted for sliding engagement with the track so that the closing plate may be moved between an open position which exposes the collection space and a closed position which encloses the collection space. Preferably, as shown in the drawings, track 366 comprises a groove in the guide plate into which the closing plate may be fitted in sliding engagement. The closing plate is attached to a carrier which is adapted to move along the support frame. Carrier 372 is preferably comprised of tubing component 374 having a first end 376 and a second end 378. In this embodiment of the invention, mounting plate 380 is attached to tubing component 374 at first end 376, and the closing plate is attached to the mounting plate. Preferably, tubing component 374 of carrier 372 is a length of square tubing that is made of steel or other suitable material. In order that tubing component 374 may easily slide outside of support frame 348, glide strips 382 are provided on the inner surface of tubing component 374.

Carrier 372 is adapted to move along support frame 348 between an open position in which the closing plate exposes the collection space and a closed position in which the closing plate encloses the collection space. Preferably, such motion is actuated by hydraulic cylinder 384 in the same manner that hydraulic cylinders 84, 184 and 284 actuate similar motion in carriers 72, 172 and 272, respectively. Hydraulic cylinder 384 includes a piston (not shown) which is attached to second end 378 of tubing component 374 of carrier 372. The cylinder is also preferably attached to support frame 348 so that extension of the piston from cylinder 384 (or retraction of the piston into cylinder 384) will move tubing component 374 of carrier 372 with respect to the support frame between an open position in which the closing plate exposes the collection space (FIG. 12) and a closed position in which the closing plate encloses the collection space (not shown). This embodiment of the invention also includes a sample extraction plate (not shown), that is similar to extraction plates 90, 190 and 290 of collectors 45, 145 and 245, respectively. This extraction plate is disposed between the guide plates and is adapted to push the sample out of the collection space in much the same way that sample extraction plate 90 pushes a sample out of the collection space of collector 45. Collector 345 also includes heater 397 that is provided in top plate 363.

Although this description contains many specifics, these should not be construed as limiting the scope of the invention but as merely providing illustrations of some of the presently preferred embodiments thereof, as well as the best mode contemplated by the inventor of carrying out the invention. The invention, as described herein, is susceptible to various modifications and adaptations, and the same are intended to be comprehended within the meaning and range of equivalents of the appended claims.

What is claimed is:

1. A sample collector for aggregate material, comprising:
   (a) a support frame having a first end and a second end;
   (b) a pair of guide plates which are attached to the first end of the support frame, said guide plates being spaced apart so as to define a collection space therebetween, at least one of said guide plates being provided with a track that extends generally along the periphery of the collection space;
   (c) a flexible closing plate which is disposed between the guide plates and adapted for sliding engagement with the track so that the closing plate may be moved between an open position which exposes the collection space and a closed position which encloses the collection space;
   (d) means for sliding the closing plate between an open position which exposes the collection space and a closed position which encloses the collection space.

2. The sample collector of claim 1 wherein the means for sliding the closing plate comprises a hydraulic cylinder.

3. The sample collector of claim 1 wherein the support frame is comprised of a length of tubing having a pair of generally planar sides, each of which is disposed generally parallel to the other.

4. The sample collector of claim 1 wherein the closing plate is attached to a carrier that is in sliding engagement with the support frame.

5. The sample collector of claim 1 wherein the track comprises a groove in which an edge of the closing plate may slide.

6. The sample collector of claim 1 wherein each of the guide plates is provided with a track that extends generally along the periphery of the collection space, which tracks are generally parallel to each other, and wherein the flexible closing plate which is disposed between the guide plates is adapted for sliding engagement with each track so that the closing plate may be moved between an open position which exposes the collection space and a closed position which encloses the collection space.

7. A sample collector assembly for use in sampling aggregate material from a truck having an open bed, said assembly comprising:
   (a) an assembly frame which includes an overhead rail that is suspended over and adjacent to a truck zone into which the truck has been driven;
   (b) a carriage which is adapted to ride on the overhead rail between a first position adjacent to the truck zone and at least one sampling position over the truck zone;
   (c) means for moving the carriage between the first position and at least one sampling position over the truck zone;
   (d) a sample collector which is attached to the carriage and which comprises:
      (i) a support frame having a first end and a second end;
      (ii) a pair of guide plates which are attached to the first end of the support frame, said guide plates being spaced apart so as to define a collection space therebetween, at least one of said guide plates being provided with a track that extends generally along the periphery of the collection space;
      (iii) a flexible closing plate which is disposed between the guide plates and adapted for sliding engagement with the track so that the closing plate may be moved between an open position which exposes the collection space and a closed position which encloses the collection space;
      (iv) means for sliding the closing plate between an open position which exposes the collection space and a closed position which encloses the collection space;
   (e) an elongate extension which is attached to the second end of the support frame;
   (f) a boom to which the elongate extension is mounted in sliding engagement therewith;
   (g) means for moving the elongate extension from a retracted position to an extended position for inserting the collector into the aggregate material in the truck.

8. The sample collector assembly of claim 7 wherein the means for moving the carriage comprises a hydraulic cylinder.

9. The sample collector assembly of claim 7 wherein the means for moving the elongate extension comprises a hydraulic cylinder.

10. The sample collector assembly of claim 7 wherein the sample collector is pivotally attached to the carriage.

11. The sample collector assembly of claim 10 wherein the sample collector is adapted to pivot on the carriage so as to permit the probe to be inserted into the aggregate along an axis that is disposed at an angle within the range of about 30° to about 150° from the horizontal.

12. A sample collector for aggregate material, comprising:
   (a) a support frame comprised of a length of tubing having a pair of generally planar sides, each of which is disposed generally parallel to the other, said support frame having a first end and a second end;
   (b) a pair of guide plates which are attached to the first end of the support frame, said guide plates being spaced apart so as to define a collection space therebetween, with each of said guide plates being provided with a pair of tracks so that each track on a guide plate extends generally along one side of the periphery of the collection space to a common termination point, and so that the tracks on one guide plate are generally parallel to the tracks on the other guide plate;
   (c) a carrier which is adapted to move along the support frame, said carrier having a first end and a second end;
   (d) a pair of flexible closing plates which are attached to opposite sides of the carrier at its first end, each of said closing plates being disposed between the guide plates and adapted for sliding engagement with the tracks on one side of the periphery of the collection space so that the carrier may be moved between an open position in which the closing plates expose the collection space and a closed position in which the closing plates enclose the collection space;
   (e) means for moving the carrier along the support frame between an open position in which the closing plates expose the collection space and a closed position in which the closing plates enclose the collection space.

13. The sample collector of claim 12 wherein the means for moving the carrier comprises a hydraulic cylinder that is attached to the second end of the carrier.

14. The sample collector of claim 12 wherein the carrier is comprised of a length of tubing having a pair of generally planar sides, each of which is disposed generally parallel to the other.

15. The sample collector of claim 12 wherein each of the tracks:

(a) comprises a groove in the guide plate; and (b) is provided with a relief opening at the common termination point.

16. The sample collector of claim 12 which includes a heater that is associated with one of the guide plates.

17. The sample collector of claim 12 which includes a nose guard that is mounted to the guide plates adjacent to the common termination point.

18. The sample collector of claim 12 which includes a sample extraction plate that is disposed between the guide plates and which is adapted to push the sample out of the collection space.

19. The sample collector of claim 18 which includes:

(a) a wheel mounted within the support frame;

(b) a belt having a first end and a second end, the first end of which is attached to the second end of the carrier and the second end of which is attached to the sample extraction plate, said belt also being disposed around the wheel;

so that when the carrier moves along the support frame to the open position in which the closing plates expose the collection space, the extraction plate will push the sample out of the collection space.

20. The sample collector of claim 19 wherein the wheel is a sprocket and the belt is a roller chain.

\* \* \* \* \*